United States Patent [19]

Harbour

[11] Patent Number: 5,729,324
[45] Date of Patent: Mar. 17, 1998

[54] PRESBYOMETER INCLUDING LOCKSTEP MEANS

[76] Inventor: Robert C. Harbour, 3115 Brittany Pl., Pensacola, Fla. 32504

[21] Appl. No.: 535,928

[22] Filed: Sep. 28, 1995

[51] Int. Cl.⁶ .................................................. A61B 3/02
[52] U.S. Cl. .......................... 351/223; 351/234; 351/239
[58] Field of Search ................................. 351/200, 222, 351/223, 227, 229, 246, 234, 239

[56] References Cited

U.S. PATENT DOCUMENTS

| | | | |
|---|---|---|---|
| 1,384,252 | 7/1921 | Giddens | 351/229 |
| 2,171,881 | 9/1939 | Luckiesh et al. | 351/222 |
| 4,385,813 | 5/1983 | Klein et al. | 351/217 |
| 4,887,897 | 12/1989 | Nose et al. | 351/233 |
| 5,110,199 | 5/1992 | Ishiog | 351/169 |
| 5,223,864 | 6/1993 | Twisselmann | 351/233 |
| 5,486,879 | 1/1996 | Barnett | 351/223 |

*Primary Examiner*—Huy Mai
*Attorney, Agent, or Firm*—Peter Loffler

[57] ABSTRACT

A presbyometer for aid in selecting the appropriate strength of over-the-counter (OTC) reading glasses is disclosed. The device comprises a view assembly with a pair of rotational lens wheels. The lens wheels each have a plurality of spaced apart apertures, each having a lens of differing dioptric strength. A user looks through the first lens on each lens wheel toward a back plate having a visual target. The lens wheels are rotated, thereby bringing a lens of increasing Diopter strength into exposure. When the user can adequately read the stimulus, the correct level of Diopter strength correction is identified and corresponding OTC glasses are purchased. A ocular width adjustment means is also disclosed.

12 Claims, 5 Drawing Sheets

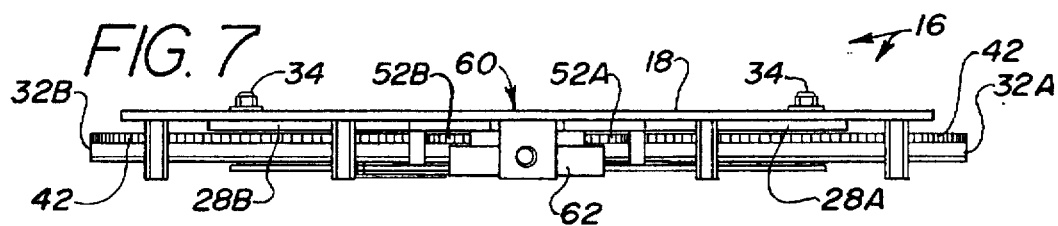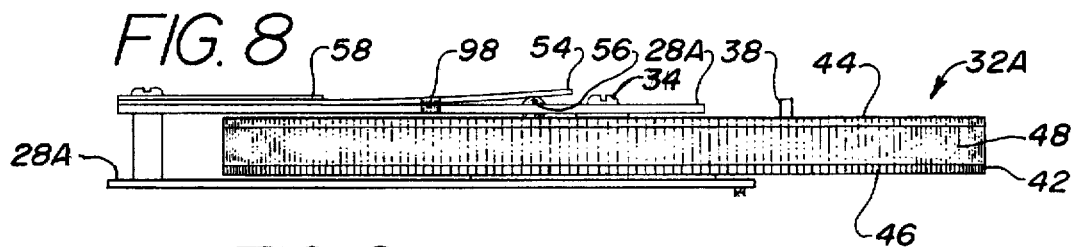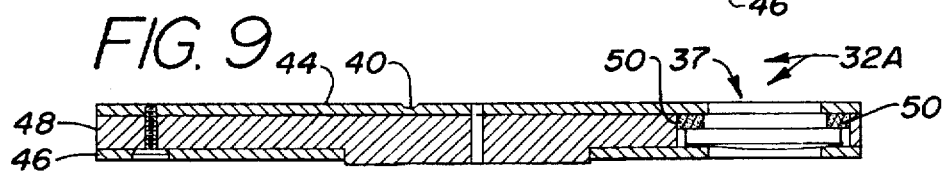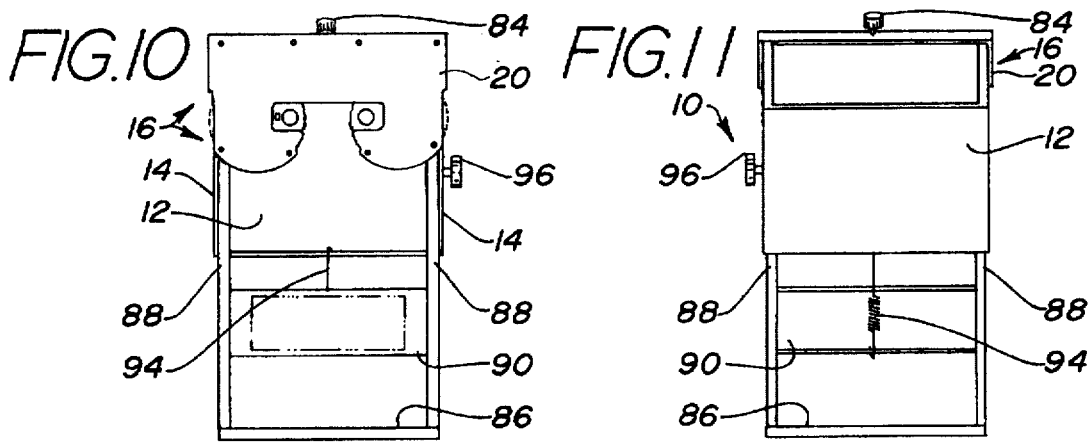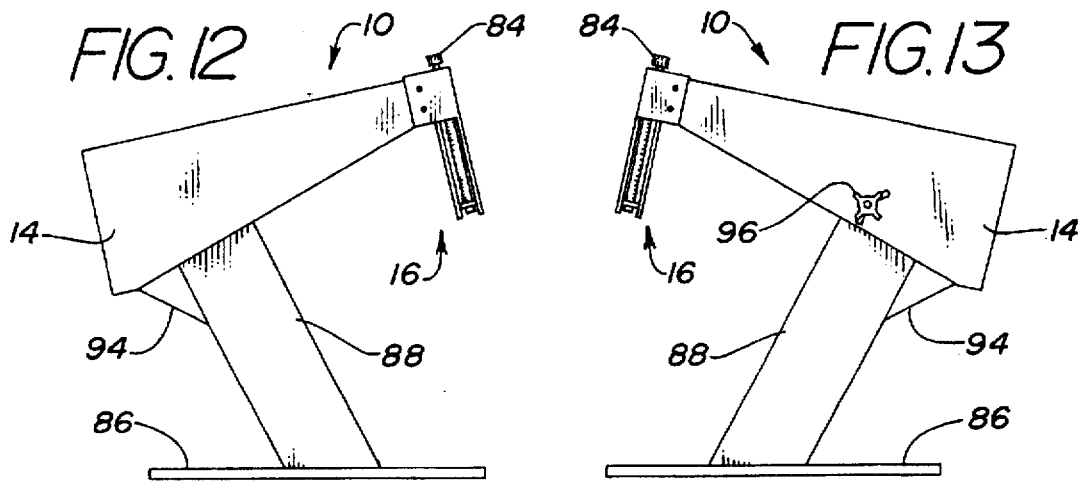

PRESBYOMETER INCLUDING LOCKSTEP MEANS

BACKGROUND OF THE INVENTION

1. Field of the Invention

The present invention relates to a device to assist lay persons in the selection of the appropriate strength reading glasses

2. Background of the Prior Art

Presbyopia is a natural, predictable (and unpreventable) aging process in which individuals gradually lose the ability to read at the normal reading distance (14–18 inches) as well as to perform tasks requiring clear vision at near (the closest point at which an individual can focus on an object). Presbyopia is the condition which results from the gradual age-related loss of accommodation; accommodation is the physiological process in which the eye focuses on objects at near. Normally, when a person fixates on an object at near, the natural lens of the eye adjusts and becomes more spherical, thereby increasing its optical power and bringing the object into focus. However, as an individual grows older, the person gradually loses the ability to accommodate, resulting in a gradually reaching near point (the closets point at which an individual can focus).

Human beings start experiencing the effects of Presbyopia (and thus losing the ability to focus at the normal reading distance) at approximately 42–44 years of age. When an individual becomes symptomatic, optical assistance for reading is needed. For individuals who wear a distance optical correction (prescription eyeglasses), the optical assistance takes the form of a second bifocal lens inserted into the lower portion of the distance glasses; the individual will read through this "bifocal" lens. For individuals who do not wear distance glasses (over half of the population), standard over-the-counter (OTC) reading glasses will compensate for presbyopic loss of accommodation. The use of these OTC reading glasses to compensate for presbyopic loss has been endorsed by the American Academy of Opthamology.

An individual who does not wear distance glasses—said to be "emmetropic"—will need to select from multiple powers of OTC reading glasses. However, this individual is not without purchasing dilemmas. Reading glasses are made in eight different optical strengths: +1.00, +1.25, +1.50, 1.75, +2.00, +2.25, +2.50, and +2.75 Diopter corrections. Initially, an emmetropic will usually start with the weakest correction (+1.00 Diopters). As the individual grows older, Presbyopia progresses, and the need for a stronger Diopter correction occurs. Many individuals, lacking an understanding of optics or visual physiology, arrive at the store and attempt to select appropriate reading glasses without actually realizing that the glasses are manufactured in varying strengths. Confused by glasses with varying power, some individuals will base the reading glasses buying decision largely on frame style, not realizing that an incorrect lens strength may result in potentially overcorrecting or undercorrecting the Presbyopic deficit.

A device is needed whereby a purchaser of OTC reading glasses can accurately select the appropriate strength of reading glasses on his own. Such a device must be easy and straightforward to use. In order to maximize its use, the device should be located at the point of sale of the OTC reading glasses.

SUMMARY OF THE INVENTION

The presbyometer of the present invention meets the above-stated need for providing a method for quickly and accurately selecting the appropriate strength of reading glasses. The device is simple to use, requiring less than two minutes to fuse and renders highly reliable results.

The device comprises a ocular viewer having a pair of corresponding lens wheels located therein. The lens wheel has a plurality of lens, each of a different Diopter strength each corresponding to a different Diopter strength. The user, beginning with a non-strength lens. The user looks through the ocular viewer at a visual stimulus located therepast. If the user cannot view the visual stimulus accurately, the user rotates the lens wheels one stop, corresponding to one level of Diopter strength increase, and again looks through the ocular viewer at the visual stimulus. The user continues in this fashion until the user can view the visual stimulus accurately. Once this happens, a legend is consulted, based on the current index number registered on the lens wheel, for the appropriate reading glasses purchase.

The lens wheels rotate in lock-step counterrotation fashion. Means are provided for increasing and decreasing the ocular width of the device for accommodating various users. The device can be fashioned in either standalone or OTC reading glass rack reception configuration.

BRIEF DESCRIPTION OF THE DRAWINGS

FIG. 7 is a top plan view of the gear coordinating mechanism.

FIG. 8 is a top plan view of the stop-click mechanism.

FIG. 9 is a section view of the lens wheel.

FIG. 10 is a front elevation view of the presbyometer in a standalone configuration.

FIG. 11 is a back elevation view of the presbyometer in a standalone configuration.

FIG. 12 is a left elevation view of the presbyometer in a standalone configuration.

FIG. 13 is a right elevation view of the presbyometer in a standalone configuration.

Similar reference numerals refer to similar parts throughout the several views of the drawings.

DETAILED DESCRIPTION OF THE PREFERRED EMBODIMENT

Figure 1:
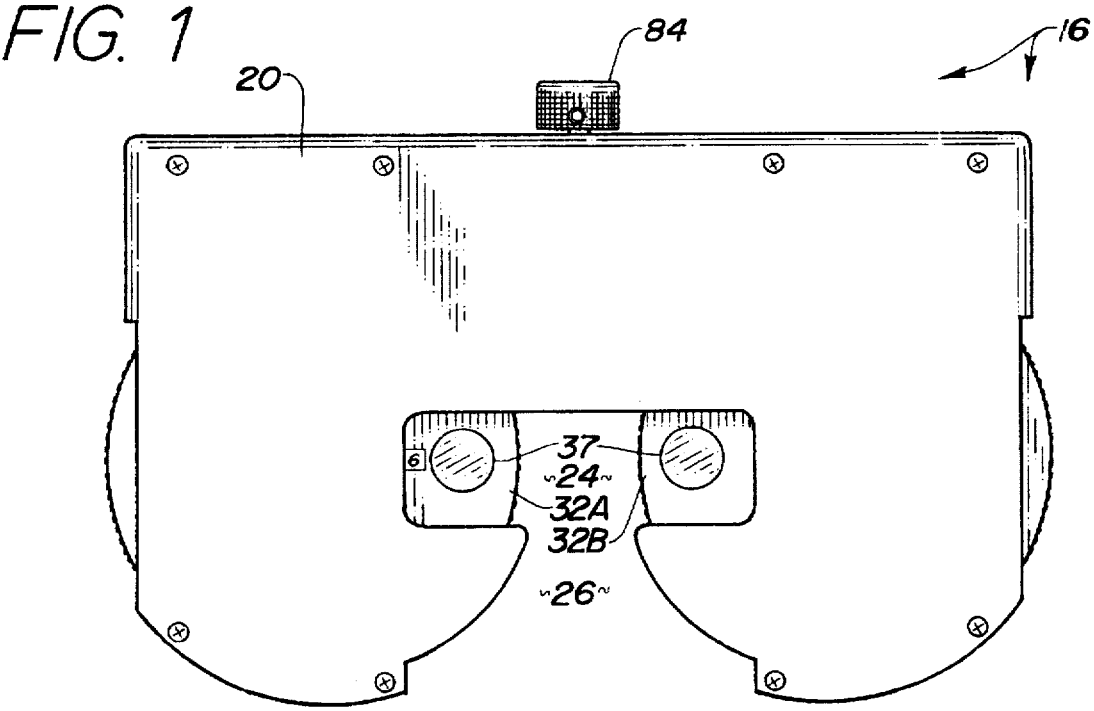
FIG. 1 is a front elevation view of the presbyometer of the present invention with the ocular width in an extended position.
Figure 2:
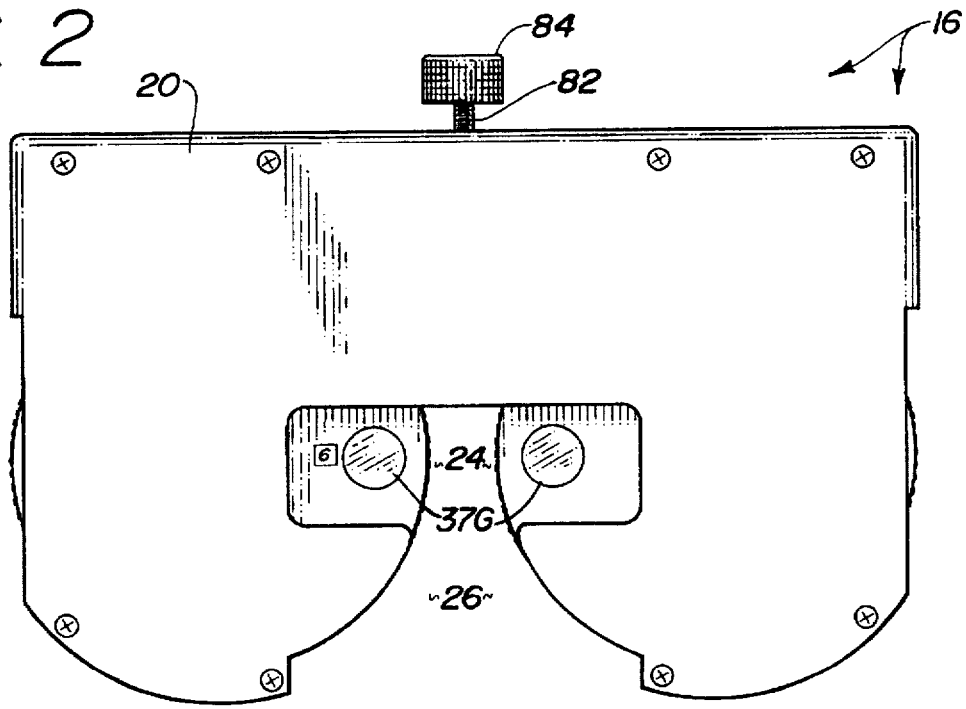
FIG. 2 is a front elevation view of the presbyometer of the present invention with the ocular width in an retracted position.

The presbyometer of the present invention comprises a frame 10. The frame 10 comprises a back plate 12, a pair of coextensive side portions 14, and a viewing assembly 16. The side portions 14 extend outwardly from either end of back plate 12. The viewing assembly 16 is attached to the ends of the side portions 14, giving the frame 10 a generally rectangular configuration. In the preferred embodiment, the back plate is located 14–18 inches away from the viewing assembly 16.

The viewing assembly 16 is comprised of an inner plate 18 and an outer plate 20 which form a rigid cross member to the horizontal frame 10. The outer plate 20 has an upper flange 22 on its upper edge which extends to the inner plate 18. The flange 22 provides protection, from dust, stray light, etc., for the mechanisms located between the outer plate 20 and the inner plate 18.

The inner plate 18 and the outer plate 20 each have a pair of laterally disposed ocular slots 24, as well as a nose relief area 26.

A pair of adjustment arms 28 are attached to the inner plate 18 at pivot points 30. The adjustment arms 28 will be denoted by reference numerals 28a and 28b. Each adjustment arm 28 can pivot about its attachment point 30. Rotatably attached to each adjustment arm 28, is a lens wheel 32. The lens wheels will be denoted by reference numerals 32a and 32b. A screw or similar stud 34 attaches each lens wheel 32 to the adjustment arm 28 with the end of each stud 34 protruding through an arced slot 36 located on the inner plate 18. Each lens wheel 32 is free to rotate about its respective attachment point. When the lens wheels 32 are installed between the outer plate 20 and the inner plate 18, the outer area of each lens wheel will extend beyond the side edges of the outer plate 20 and inner plate 18. The outer edges of the lens wheels can be slotted or knurled for easy grippability by the user.

Figure 3:
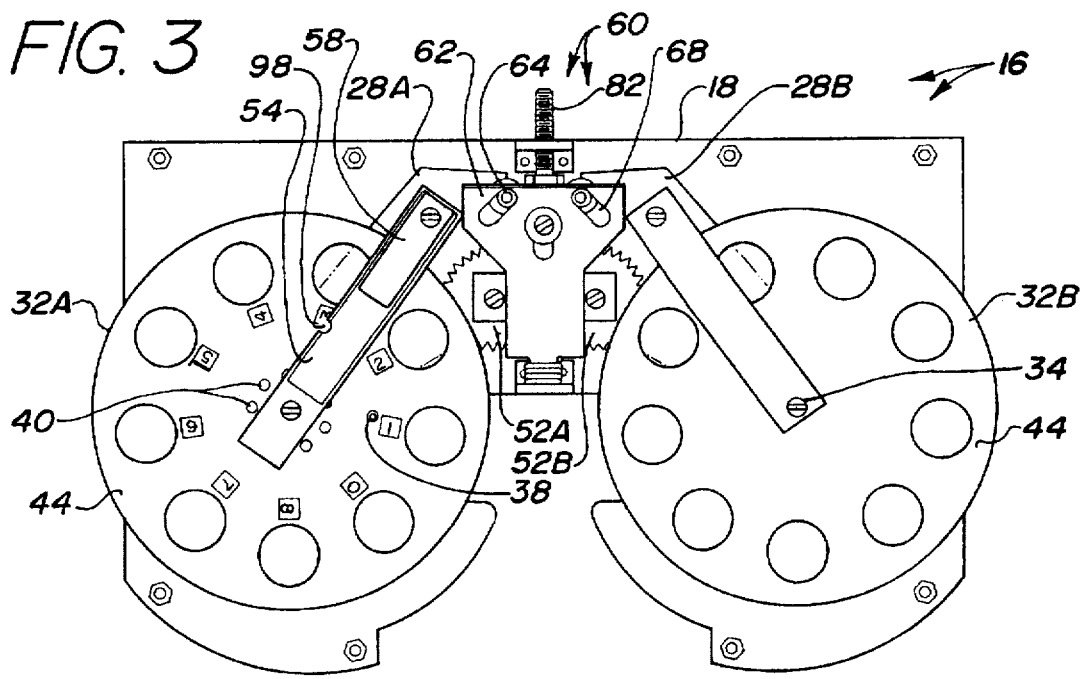
FIG. 3 is a view of FIG. 1 with the front plate removed.
Figure 4:
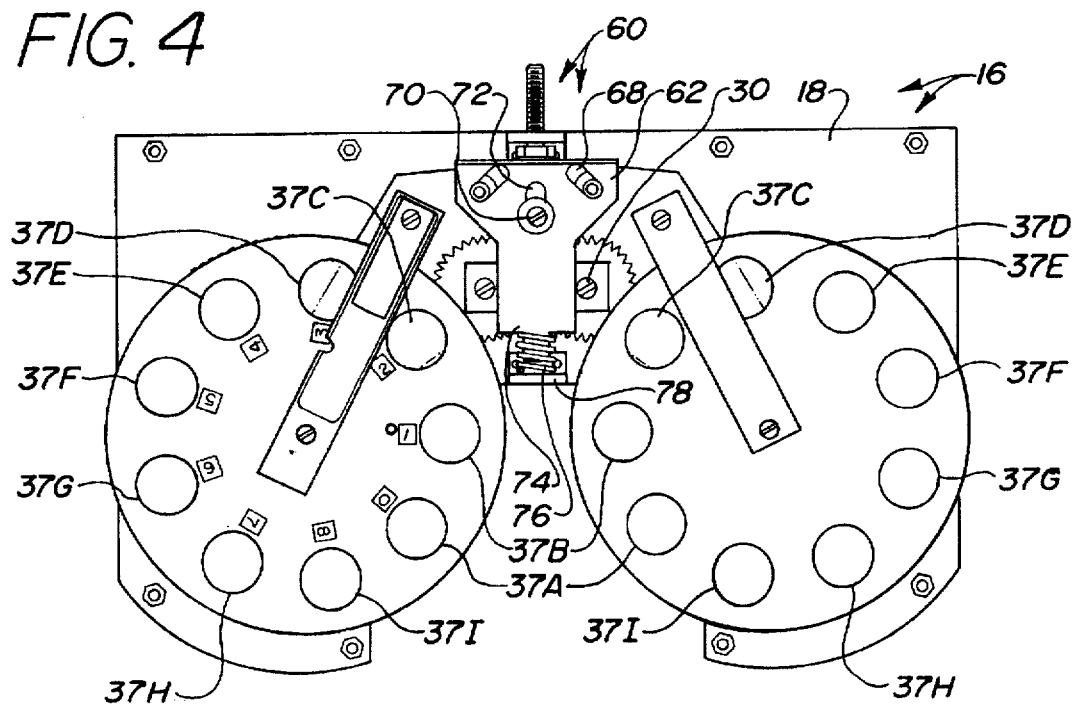
FIG. 4 is a view of FIG. 2 with the front plate removed.
Figure 5:
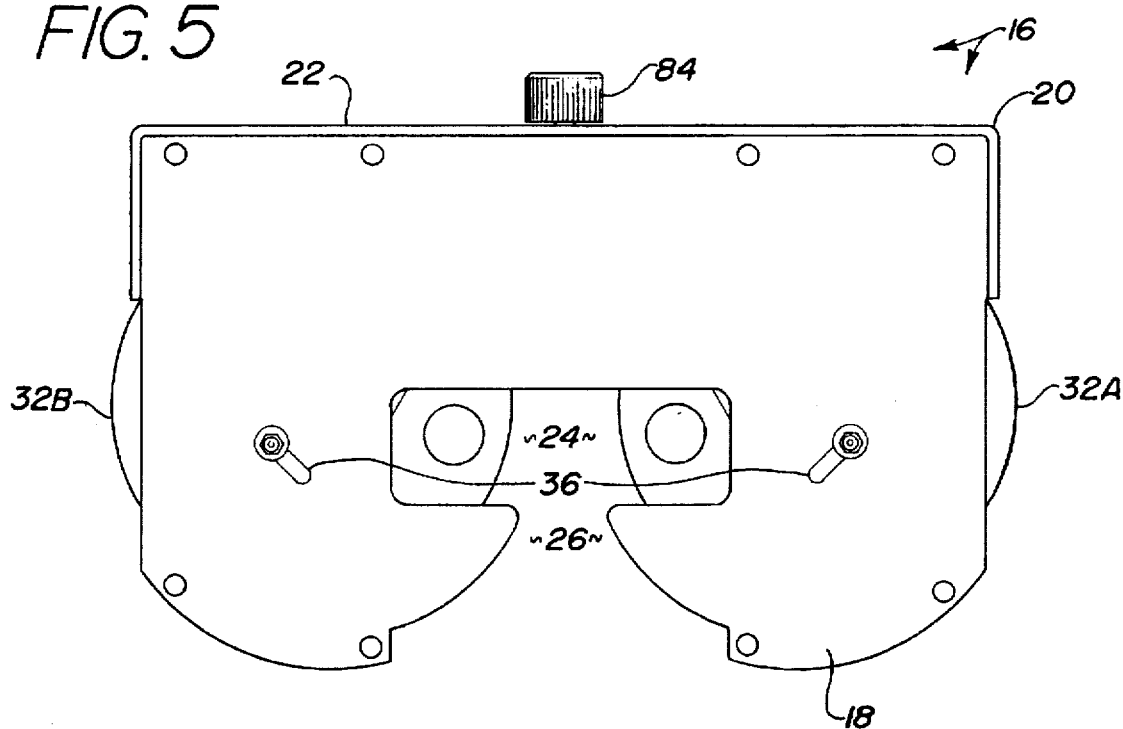
FIG. 5 is a back elevation view of the presbyometer of the present invention.
Figure 6:
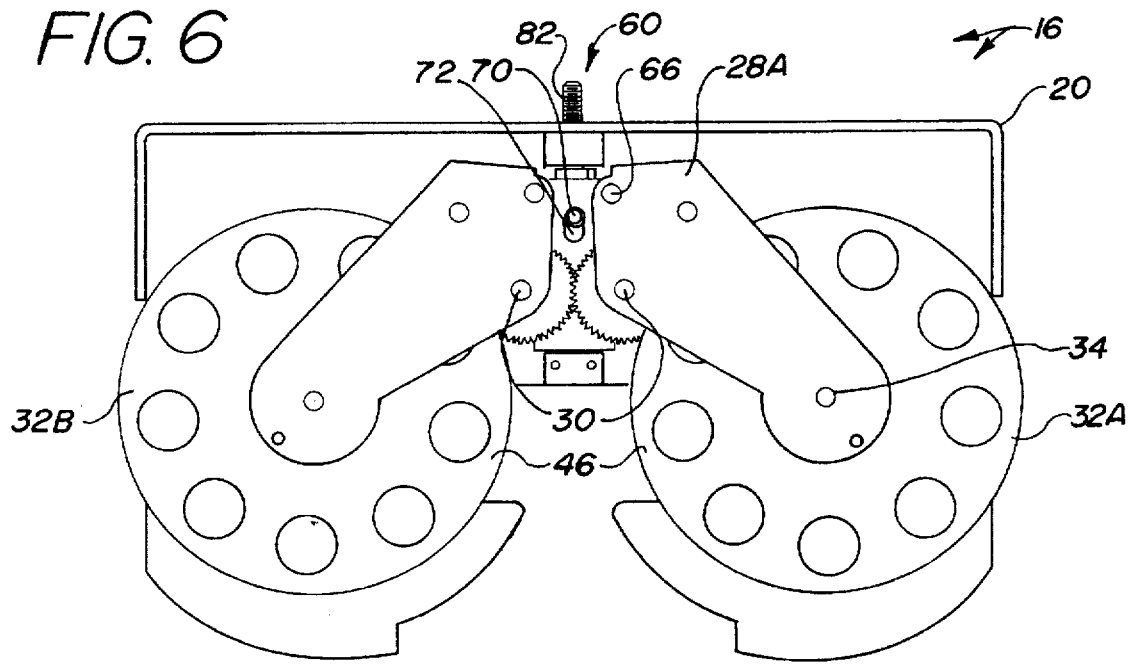
FIG. 6 is a view of FIG. 5 with the back plate removed.
Figure 14:
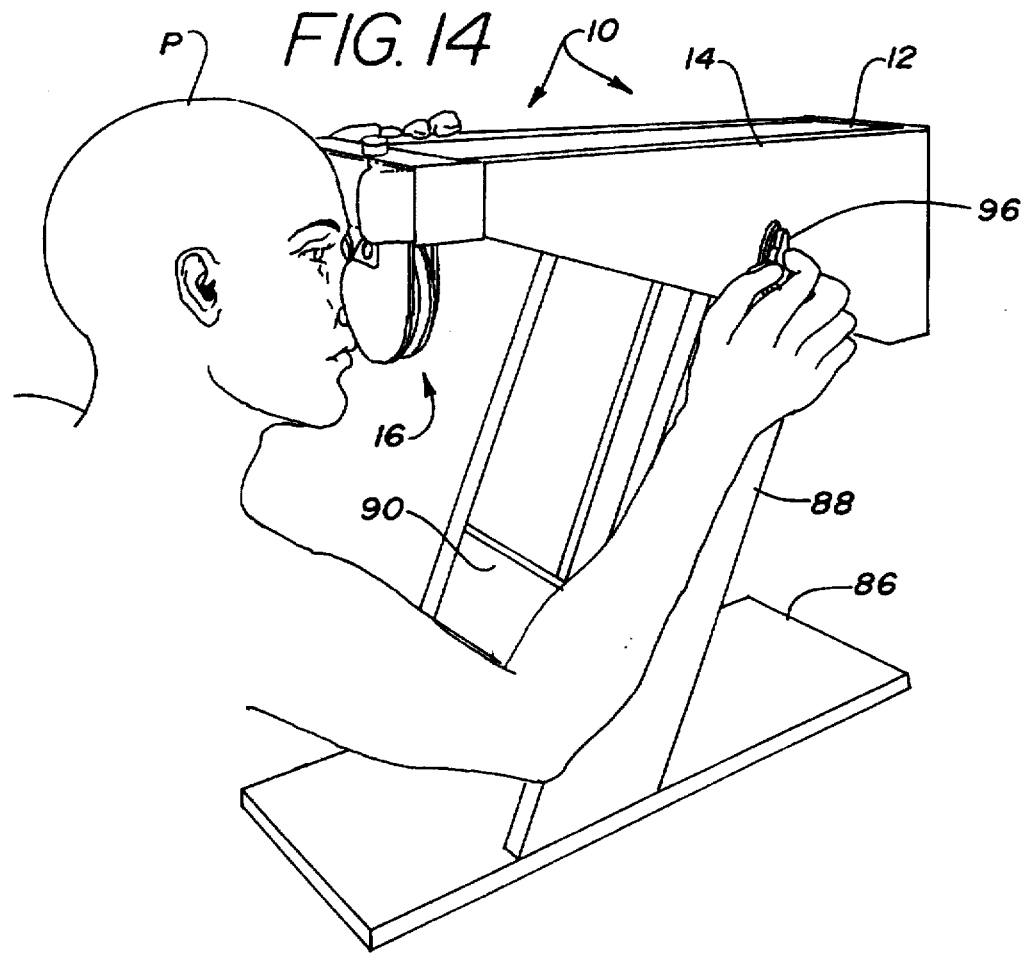
FIG. 14 is a perspective view of the presbyometer being utilized.
Figure 15:
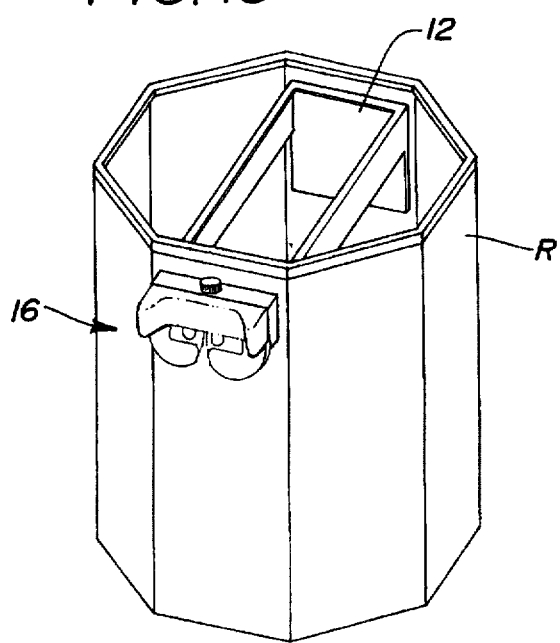
FIG. 15 is a perspective view of the presbyometer received in an OTC reading glasses rack.

Each lens wheel 32 has nine spaced apart apertures 36 denoted by reference numerals 36a–36i. As seen in FIGS. 3 and 4, the first lens wheel 32a has a number located next to each aperture beginning with the number 0 in the first aperture 36a and, proceeding in counterclockwise fashion, numbered consecutively upward to the number 8 corresponding to aperture 36. Located in apertures 36a–36g is a series of lenses with differing Diopter powers. Located in the first aperture 36a on both the first lens wheel 32a and the second lens wheel 32b is a non-strength lens. Located in the second aperture 36b on both the first lens wheel 32a and the second lens wheel 32b is a lens of strength +1.00 Diopters. Located in the third aperture 36c on both the first lens wheel 32a and the second lens wheel 32b is a lens of strength +1.25 Diopters. Located in the forth aperture 36d on both the first lens wheel 32a and the second lens wheel 32b is a lens of strength +1.50 Diopters. Located in the fifth aperture 36e on both the first lens wheel 32a and the second lens wheel 32b is a lens of strength +1.75 Diopters. Located in the sixth aperture 36f on both the first lens wheel 32a and the second lens wheel 32b is a lens of strength +2.00 Diopters. Located in the seventh aperture 36g on both the first lens wheel 32a and the second lens wheel 32b is a lens of strength +2.25 Diopters. Located in the eighth aperture 36h on both the first lens wheel 32a and the second lens wheel 32b is a lens of strength +2.50 Diopters. Located in the ninth aperture 36i on both the first lens wheel 32a and the second lens wheel 32b is a lens of strength +2.75 Diopters. As seen, the apertures and their respective lens of the second lens wheel are disposed in similar fashion except their progression is in clockwise fashion.

A raised stud 38 is located next to the imprinted number 1 on the first lens wheel 32a. This raised stud 38 engages the adjustment arm 28a when it contacts either side of the adjustment arm 28a, thereby preventing further lens wheel rotation in that direction. Also located on the first lens wheel 32a, are nine spaced apart spherical indentations 40. A gear ring 42 is located on each lens wheel 32.

As seen in FIG. 9, each lens is sandwiched within a front plate 44 and a rear plate 46 comprising the lens wheel 32. A body member 48 separates the front plate 44 from the rear plate 46. The lens is held in place within its aperture by use of an open or closed-cell foam or other suitable cushioning material 50.

Rotatably mounted to each adjustment arm 28 is a coordinating gear 52. The gears will be denoted by reference numerals 52a and 52b. Each gear is identical to the other and the two gears are continually meshed with one another. The first gear 52a is also meshed with the gear ring 42 of the first lens wheel 32 while the second gear 52b is meshed with the gear ring 42 of the second lens wheel 32b. Rotation of one of the lens wheels, will cause that lens wheel's gear ring 42 to engage its respective gear 52 which in turn will engage the other gear, which in turn engage the gear ring 42 of the other lens wheel causing the other lens wheel to rotate in lockstep, in counter-rotation fashion, with the rotated lens wheel.

As seen in FIGS. 3, 4 and 8, the first adjustment arm 28 has an index spring 52, which is a flat spring member. Located underneath the front end of the index spring 54 is an index bearing 56. The index bearing 56 protrudes through an aperture (not shown) on the first adjustment arm 28 and contacts the front plate 44 of the first lens wheel 32a. An index spring retainer plate 58, which is a rigid plate member, is affixed to the top of the rear end of the index spring 54 in order to help clamp the index spring 54 down.

When the lens wheels 32a and 32b are rotated, the bearing 56 will align with, and will partially drop into one of the spherical indentations 40 located on the first lens wheel 32. This alignment occurs each time one set of corresponding lens is aligned with its respective ocular slot 24. The bearing 56 will be held within the spherical indentation 40 by the index spring 54 thereby preventing rotation of the lens wheels. This provides the lens wheels 32 with a friction "click-stop."

Also located within the viewing assembly 16 is an ocular width adjustment control 60. The ocular width adjustment control 60 comprises a bracket 62. The bracket 62 is mounted on two studs 64. One stud 64 each is attached to an adjustment arm 28 at point 66, and protrudes through diagonally disposed elongated slots 68 located on the bracket 62. Holding the bracket 62 in place against the inner plate is a screw 70 that protrudes through a vertically disposed elongated slot 72 on the bracket 62. Located at the base 74 of the bracket 62 is a coil spring 76. One end of the spring 76 biases against the base 74 of the bracket 62 while the opposing end of the spring 76 biases against a lower flange 78 that extends outwardly from the outer plate 20. Attached to the top 80 of the bracket 62 is a threaded stud 82. The threaded stud 82 protrudes through the upper flange 22 of the outer plate 20. A second adjustment knob 84 is threadly attached to the threaded stud 82.

When the second adjustment knob 84 is rotated clockwise, the threaded stud 82 proceeds downward, which in turn pushes the bracket 62 downward. This causes each stud 64 to travel up its respective elongated slot 68. The screw 70, travels within its elongated slot 68 and does not impede this operation. This causes the upper end of each adjustment arm 28 to be brought closer to one another. By pivoting about its attachment point 30, the lower end of each adjustment arm 28 swings outward. This action pushes each lens wheel 32 farther apart from one another thereby increasing the lateral distance the two exposed lens.

In order to decrease the ocular width, the second adjustment knob 84 is rotated counterclockwise. This causes the bracket 62, due to the biasing of the compressed coil spring 76, to be raised upward. This causes each stud 64 to travel down its respective elongated slot 68. Again, the screw 70, travels within its elongated slot 72 and does not impede this operation. This causes the upper end of each adjustment arm 28 to be farther apart from one another. By pivoting about attachment point 30, the lower end of each adjustment arm 28 swings inward. This action pushes each lens wheel 32 closer together thereby increasing the distance between the exposed lens on the first lens wheel 32 relative to the exposed lens on the second lens wheel 32.

The capped stud 34 that attaches each lens wheel travels through its elongated slot 36 and does not impede the above operation. The device is designed so that when the device is adjusted to its widest ocular width, a particular lens on each wheel and the associated reference numeral on the first lens wheel 32a is exposed within the respective ocular slots on the inner plate 18 and the outer plate 20. The device is also designed so that when the device is adjusted to the narrowest ocular width, the ends of each lens wheel extend beyond the sides of the inner plate 18 and the outer plate 20.

The device can be inserted directly into a OTC glasses frame rack. The device is securely attached into the inner portion of the rack.

Alternately, the device can be designed to be freestanding. Included in this alternate embodiment, is a base 86 having a pair of vertical supports 88. A cross member 90 extends between the pair of vertical supports 88, providing torsional rigidity. Pivotally attached to the top of the vertical supports 88 is the frame 10.

One end of a coil tension spring 94 is attached to the lower portion of the back plate 12 while the opposing end of the coil tension spring 94 is attached to the cross member 90. As the viewing assembly is relatively heavy and the frame 10 is free to pivot about the radial axis, relative to its points of attachment to the vertical supports 88, the coil spring 94 provides counter-balance to the frame 10. Alternately, a counterweight, of suitable mass, can be affixed to the frame in proximity to the back plate 12 thereby dispensing with the need for the coil spring.

In order to adjust the height of the viewing assembly 16, the viewing assembly 16 can be pulled down to the desired height. A threaded shaft (not shown) protrudes out through an arc-shaped slot located on one of the arms 28 of the horizontal frame. A first knob 96 is attached to the end of the threaded shaft. Rotating the knob 96, clamps it into the arm 28 of the frame 10, thereby holding the frame 10 stationary.

In order to use the device of the present invention, a user first adjusts the height of the viewing assembly 16 (if a base-mounted embodiment is used) by loosening the first knob 96 and pivoting the viewing assembly 16 to the desired height and thereafter tightening the first knob 96. Thereafter the user selects the appropriate ocular width of the two lens wheels. This is performed by the turning of the second knob 84 desired.

One of the lens wheels is rotated so that the first lens—the plano (non-strength) lens located in aperture 36a and bearing reference numeral 0, is exposed. The raised stud contacts the side of the adjustment arm to prevent further rotation of the lens wheels when this first lens is exposed. An optional small slotted portion 98 can be located on the first adjustment arm and index spring 54, on either or both sides, to assure proper lens alignment within the ocular slot 24. The raised stud 34 enters the optional small slotted portion 98, in order to permit slight further lens wheel rotation in order to achieve the lens-ocular slot alignment.

The plano (non-strength) lens corresponds to the user's current vision situation. The user looks through the exposed lens toward the back plate 12 of the frame 10. Affixed to the back plate 12 will be a visual stimulus preferably some form of reading material. The back plate will be located at the normal reading distance of 18 inches away from the viewing assembly 16.

If the user looks through the non strength plano lens and can read clearly, then reading glasses are not called for. If the user cannot read clearly, then one of the lens wheels is rotated to bring the lens with reference numeral 1 into exposure. When the next lens is exposed, the first lens wheel will click-stop. If the user can now read clearly, then lens number 1 is called for. A legend located on or near the device will tell the user that lens number 1 corresponds to reading glasses of strength +1.00 Diopters, and the user will select glasses of that strength from the glasses rack. If user cannot reading clearly after looking through lens number 1, one of the lens wheels is rotated to bring the lens with reference numeral 2 into exposure. If the user can now read clearly, then lens number 2 is called for. Again the legend is consulted in order to select the appropriate strength of glasses. If lens number 2 is insufficient, the user proceeds through the remaining lens, in sequential order, until he arrives at the first lens through which he can read clearly. The user checks the legend for the correct strength glasses and makes a purchase. If the user still does not read clearly after reach lens number 8 (+2.75 Diopters), then instructions on or near the device would advise the person that OTC reading glasses are not the source of solution for the user's reading difficulty and that medical attention should be sought.

While the invention has been particularly shown and described with reference to an embodiment thereof, it will be understood by those skilled in the art that various changes in form and detail may be made without departing from the spirit and scope of the invention.

I claim:

1. A presbyometer comprising:
   a first plate and a second plate each having ocular openings for two eyes, an indentation for a nose, a top, and a pair of sides;
   a first adjustment arm and a second adjustment arm each pivotally attached to one of the pair of plates;
   a first lens wheel, having a first set of optical lens of differing optical strengths, rotatably attached to the first adjustment arm and extending beyond one of the sides of the first plate and the second plate and a second lens wheel, having a second set of optical lens in similar optical strengths to the optical strengths of the first set of optical lens, rotatably attached to the second adjustment arm and extending beyond the other of the sides of the first plate and the second plate;
   a visual stimulus, disposed in spaced apart relation to the first plate and the second plate and in the visual path of the ocular openings; and
   lockstep means for rotating, in equal and opposite angular distance, one of the first lens wheel or the second lens wheel when the other of the first lens wheel or the second lens wheel is rotated.

2. The presbyometer as in claim 1 to further include a head rest, located on the first plate, for receiving a user's head when utilizing the presbyometer.

3. The presbyometer as in claim 1 to further include a base, for pivotally receiving the first plate and the second plate.

4. The presbyometer as in claim 1 wherein the presbyometer is adapted to be received within a reading glasses rack.

5. The presbyometer as in claim 1 wherein the first set of optical lens has optical lens in strengths of 0.00, +1.00, +1.25, +1.50, +1.75, +2.00, +2.25, +2.50, and +2.75 Diopters and the second set of optical lens has optical lens in strengths of 0.00, +1.00, +1.25, +1.50, +1.75, +2.00, +2.25, +2.50, and +2.75 Diopters.

6. The presbyometer as in claim 1 further comprising adjustment means for adjusting the lateral separation between the first lens wheel and the second lens wheel.

7. The presbyometer as in claim 6 wherein the adjustment means is comprised of a pivot means for adjusting the lateral separation between the first adjustment arm and the second adjustment arm.

8. The presbyometer as in claim 7 wherein the pivot means comprises:
- a bracket having a first elongated slot sloping diagonally upwardly and a second elongated slot sloping diagonally downwardly;
- a first stud attached to the first adjustment arm and protruding through the first slot and a second stud attached to the second adjustment arm and protruding through the second slot;
- a lower flange extending from either the first plate or the second plate;
- a coil spring having a first end abutting the lower flange and a second end abutting the bracket;
- an upper flange connecting the first plate and the second plate;
- a threaded stud attached to the bracket and extending through the upper flange; and
- wherein rotation of the threaded stud causes downward articulation of the bracket against the coil spring and upward articulation of the first stud to the top of the first slot and upward articulation of the second stud to the top of the second slot pivoting the first lens wheel and the second lens wheel away from each other and counterrotation of the threaded stud causes upward articulation of the bracket due to the bias of the coil spring and downward articulation of the first stud to the bottom of the first slot and downward articulation of the second stud to the bottom of the second slot pivoting the first lens wheel and the second lens wheel toward each other.

9. The presbyometer as in claim 1 wherein the lock step means comprises:
- a first gear ring attached to the first lens wheel;
- a second gear ring attached to the second lens wheel; and
- a gear assembly, meshed with the first gear ring and the second gear ring.

10. The presbyometer as in claim 1 further comprising alignment means for aligning one of the optical lens from the first lens wheel and one of the optical lens from the second lens wheel within the ocular openings.

11. The presbyometer as in claim 10 wherein the alignment means comprises;
- a plurality of indentations disposed on the first lens wheel, one indentation each for each of the optical lens;
- a bearing disposed within an opening on the first adjustment arm;
- an index spring, attached to the first adjustment arm, for retaining the bearing within the opening; and
- whereby when the first lens wheel is rotated, the bearing will drop into one of the plurality of indentation and remain biased therein by the index spring when one of the optical lens from the first lens wheel and one of the optical lens from the second lens wheel is aligned within the ocular openings.

12. The presbyometer as in claim 1 further comprising stop means for preventing full 360-degree rotation of the first lens wheel.

* * * * *